United States Patent
Kukuk (10) Patent No.: US 7,277,833 B2
(45) Date of Patent: Oct. 2, 2007

(54) MODELING OF THE WORKSPACE AND ACTIVE PENDING BEHAVIOR OF AN ENDSCOPE USING FILTER FUNCTIONS

(75) Inventor: Markus Kukuk, Princeton, NJ (US)

(73) Assignee: Siemens Corporate Research, Inc., Princeton, NJ (US)

( * ) Notice: Subject to any disclaimer, the term of this patent is extended or adjusted under 35 U.S.C. 154(b) by 707 days.

(21) Appl. No.: 10/102,580

(22) Filed: Mar. 20, 2002

(65) Prior Publication Data

US 2003/0182091 A1 Sep. 25, 2003

Related U.S. Application Data

(63) Continuation-in-part of application No. 10/072,574, filed on Feb. 6, 2002, now Pat. No. 7,179,220.

(51) Int. Cl.
*G06F 17/00* (2006.01)
*A61B 1/00* (2006.01)
(52) U.S. Cl. ............... 703/2; 600/101; 600/114; 600/117; 600/118; 600/139; 600/145
(58) Field of Classification Search .............. 703/6, 703/2; 600/114, 117, 118, 145, 101, 139
See application file for complete search history.

(56) References Cited

U.S. PATENT DOCUMENTS 4,737,142 A * 4/1988 Heckele ............... 604/95.04
5,035,231 A * 7/1991 Kubokawa et al. ......... 600/109
5,289,373 A * 2/1994 Zarge et al. ................ 600/434
5,482,029 A * 1/1996 Sekiguchi et al. .......... 600/109
5,766,016 A * 6/1998 Sinclair et al. ............. 434/262
5,836,869 A * 11/1998 Kudo et al. ................ 600/173
5,885,207 A * 3/1999 Iwasaka ..................... 600/139
5,888,193 A * 3/1999 Breidenthal et al. ........ 600/160
5,935,139 A * 8/1999 Bates ......................... 606/159
5,964,715 A   10/1999 Thunberg ................... 600/562
6,097,994 A    8/2000 Navab et al. ............... 700/245
6,205,411 B1 * 3/2001 DiGioia et al. .............. 703/11
6,249,713 B1   6/2001 Geiger et al. ............... 700/57
6,272,371 B1 * 8/2001 Shlomo ...................... 600/424
6,346,940 B1 * 2/2002 Fukunaga ................... 345/427

(Continued)

OTHER PUBLICATIONS

K. Ikuta, M. Takeichi, and T. Namiki, "Virtual Endoscope System with Force Sensation," 1999 IEEE, pp. 1715-1721.*

(Continued)

*Primary Examiner*—Hugh Jones
*Assistant Examiner*—Kibrom K. Gebresilassie
(74) *Attorney, Agent, or Firm*—Donald B. Paschburg; F. Chau & Associates, LLC (57) ABSTRACT

A method is provided for simulating a flexible tube in an environment. The method comprises determining a model of the flexible tube according to a plurality of internal constraints of the flexible tube and a plurality of external constraints of the flexible tube, determining a workspace of the flexible tube according to a model of the flexible tube, and determining a model of an active bending behavior of a tip of the flexible tube.

12 Claims, 3 Drawing Sheets

U.S. PATENT DOCUMENTS

| | | | |
|---|---|---|---|
| 6,623,424 B2* | 9/2003 | Hayakawa et al. | 600/139 |
| 6,669,629 B2* | 12/2003 | Matsui | 600/152 |
| 6,936,003 B2* | 8/2005 | Iddan | 600/114 |
| 7,179,220 B2* | 2/2007 | Kukuk | 600/101 |
| 7,199,545 B2* | 4/2007 | Oleynikov et al. | 318/568.12 |
| 2002/0028984 A1* | 3/2002 | Hayakawa et al. | 600/139 |
| 2002/0059284 A1* | 5/2002 | Bronstein et al. | 707/100 |
| 2002/0133057 A1* | 9/2002 | Kukuk | 600/101 |
| 2004/0152971 A1* | 8/2004 | Kukuk | 600/424 |

OTHER PUBLICATIONS

R. Gayle, M. C. Lin, and D. Manocha, "Constraint-Based Motion Planning of Deformable Robots," University of North Carolina.*

E. Anshelevich, S. Owens, F. Lamiraux, and L. E. Kavraki, "Deformable Volumes in Path Planning Application," Proceedings of the 2000 IEEE, pp. 2290-2295.*

K. Ikuta, K. Iritani, and J. Fukuyama, "Portable Virtual Endoscope System with Force and visual Display for Insertion Training," MICCAI 2000, LNCS 1935, pp. 907-920, 2000.*

K. Ikuta, M. Takeichi, and T. Namiki, "Virtual Endoscope System with Force Sensation," Proceedings of the 1999 IEEE.*

H. Zou, K. A. Malek, and J. Y. Wang, "Computer-aided design using the method of cut-joint kinematic constraints" 1996 Elsevier Science Ltd., pp. 796-806.*

W. Verdonck, J. Swevers, X. Chenut, and J. C. Samin, "Combining Internal and External Robots Models to Improve Models Parameter Estimation," 2001 IEEE.*

B. Geiger, "Real-Time Collision Detection and Response for Complex Envrinoments," 2000 IEEE, 9 pages.*

Markus Kukuk, *Modeling the Internal and External Constraints of a Flexible Endoscope for Calculating its Workspace: Application in Transbronchial Needle Aspiration Guidance*, SPIE International Symposium on Medical Imaging, San Diego, CA, Feb. 23-28.

Kukuk M.: "Modeling the Internal and External Constraints of a Flexible Endoscope for Calculating Its Workspace: Application in Transbronchial Needle Aspiration Guidance" Proceedings of the SPIE, SPIE, Bellingham, VA, US, vol. 4681, Feb. 24, 2002, pp. 539-550, XP008021047 p. 540, line 16 -p. 549, line 12.

Campos T P R: "Connectionist Modeling for Arm Kinematics Using Visual Information" IEEE Transactions on Systems, Man and Cybernetics. Part B: Cybernetics,IEEE Service Center, US, vol. 26, No. 1, Feb. 1, 1996, pp. 89-99, XP000582904 ISSN: 1083-4419.

* cited by examiner

MODELING OF THE WORKSPACE AND ACTIVE PENDING BEHAVIOR OF AN ENDSCOPE USING FILTER FUNCTIONS

This is a continuation-in-part of Ser. No. 10/072,574 entitled "METHOD FOR GUIDING FLEXIBLE INSTRUMENT PROCEDURES," Now U.S. Pat. No. 7,179,220, filed Feb. 6, 2002.

BACKGROUND OF THE INVENTION

1. Field of the Invention

The present invention relates to modeling a workspace and, more particularly, to modeling the workspace of a device according to internal and external constraints.

2. Discussion of Related Art

Deformable models have been implemented in computer graphics and animation, in surgery simulation (deformable tissues), and in medical imaging (model-based segmentation). However, no known system or method exists for modeling the mechanical details and bending characteristics of an endoscope and the calculation of its workspace.

A model of an endoscope has been described as a part of a virtual endoscope system and method with force sensation. The model includes a collection of rigid links, interconnected by joints. To achieve real-time simulation, a simplified Newton-Euler equation of motion can be used. The simplified Newton-Euler equation disregards velocity and acceleration. A small number of joints are used as part of the virtual endoscope system, with increasing length from the endoscope tip to the head, which limits the accuracy of the model. Since the method is a simulator, for educational purposes, the emphasis is more on visual and palpable correctness than on millimeter accuracy.

Another method proposes a deformable model for long, thin instruments like catheters. A snake approach has been used. The shape of the catheter is represented by a fourth order B-spline, the control points of the B-spline are moved in an optimation process, to find a minimum energy representation.

One limitation of these models is that the special mechanics of the endoscope bending section have not been taken into account. Thus, the accuracy of the model can be difficult to maintain.

Therefore, a need exists for a method of modeling the internal and external constraints of a flexible endoscope for determining a workspace.

SUMMARY OF THE INVENTION

According to an embodiment of the present invention, a method is provided for simulating a flexible tube in an environment. The method comprises representing the flexible tube in the environment according to a model, and determining a model of the flexible tube according to a plurality of internal constraints of the flexible tube and a plurality of external constraints of the flexible tube. The method further comprises determining a workspace of the flexible tube according to a model of the flexible tube, and determining a model of an active bending behavior of a tip of the flexible tube.

The model of the flexible tube is a chain of rigid links, interconnected by discrete joints.

The workspace is a spatial tree, wherein the growth of the spatial tree is controlled by one or more filter functions.

The spatial tree is a tree data structure comprising a plurality of nodes, wherein each node represents a joint in three-dimensional space. The spatial tree is a tree data structure comprising a plurality of edges, wherein each edge connects a node with its child and represents a link in three-dimensional space. The spatial tree is a tree data structure comprising a plurality of paths, wherein each path from a root to a leaf represents a flexible tube, and wherein all paths from the root to the leafs represent the workspace of the modeled flexible tube under a plurality of constraints.

The method further comprises determining the filter functions, wherein determining the filter functions comprises the step of determining at least one of a geometry filter, a joint filter, a bounding tube filter, a gravity filter, and a stopping criteria filter. The method further comprises building the spatial tree, wherein building the spatial tree comprises determining an interaction of the flexible tube with the environment, and determining a length of the flexible tube to a target. Building the spatial tree further comprises determining a length for each link of the flexible tube, determining a diameter for each link of the flexible tube, determining a maximum angle for each joint of the flexible tube, and restricting the workspace to a portion of the environment.

The spatial tree is built one of recursively and iteratively.

Determining a model for the active bending of the flexible tube's tip comprises finding the center of a circle that best approximates the movement of the tip.

The flexible tube is one of an endoscope and a catheter.

According to an embodiment of the present invention, a program storage device is provided, readable by machine, tangibly embodying a program of instructions executable by the machine to perform method steps for simulating a flexible tube in an environment. The method comprises determining a model of the flexible tube according to a plurality of internal constraints of the flexible tube and a plurality of external constraints of the flexible tube, determining a workspace of the flexible tube according to a model of the flexible tube, and determining a model of an active bending behavior of a tip of the flexible tube.

According to an embodiment of the present invention, a method is provided for modeling a workspace of a flexible tube. The method comprises determining a joint filter according to a flexibility of the tube, determining a geometry filter according to an interaction of the tube with its physical confines, and determining a gravity filter. The method further comprises determining a bounding tube filter according to a portion of the physical confines in which the tube has been inserted, and determining a stopping criteria filter according to one of a dock or a tube length. The method comprises representing a model of the workspace of the flexible tube.

Determining a joint filter comprises determining a maximum joint angle according to a position of a joint within a chain of interconnected links, wherein the flexible tube is modeled as the chain of interconnected links.

The method comprises determining a model of the physical confines.

Determining a bounding tube filter limits the workspace to a portion of the physical confines.

The stopping criteria is a number of links of the flexible tube needed to reach a target site. The stopping criteria is fulfilled upon determining a dock between a link and the target site.

BRIEF DESCRIPTION OF THE DRAWINGS

Preferred embodiments of the present invention will be described below in more detail, with reference to the accompanying drawings:

FIG. 3b is a graph of joint range functions corresponding to FIG. 3a;

FIG. 4b is a graph of joint range functions corresponding to FIG. 4a;

DETAILED DESCRIPTION OF PREFERRED EMBODIMENTS

Transbroncial needle aspiration (TBNA) is a valuable minimally invasive procedure in the bronchosdopic diagnosis and staging of patients with lung cancer. The procedure allows non-surgical access to lymph nodes from the inside of the tracheobronchial tree. Traditionally this biopsy is performed by maneuvering an endoscope to a suitable site within the tracheobronchial tree. Then the surgeon inserts a needle through the endoscope and punctures the bronchial wall to hit a target behind the wall. This is a blind puncture since the target object is not visible be the endoscope. If the bronchial wall is not yet affected, the failure rate can be between about 60 to 80%.

In robotics, the term "workspace" denotes that volume of space which the end-effector of a robot can reach. Similarly, the workspace of a flexible endoscope is the volume of space that can be occupied by the entire endoscope. From the endoscope's perspective, the workspace can be determined by its internal mechanical constraints, as well be its external constraints, for example, organ geometry and gravity. According to an embodiment of the present invention, the workspace of an endoscope can be determined under insertion into a patient specific organ model. A method according to the present invention provides a model of an endoscope that takes the internal constraints into account. A method which simulates the insertion of an endoscope into an organ is also provided. The method determines the workspace by recursively building a spatial tree whose growth can be constrained by a series of filter functions. Knowledge of an endoscope's workspace can be used to assess the accuracy of a model by comparing it to a real endoscope in a test environment.

According to an embodiment of the present invention, a model E can be configured to represent any given endoscope. The model E represents an endoscope as a chain of rigid links, interconnected by discrete ball and socket joints. A link can be represented by a cylinder of a given length and diameter. A method AE can be provided that determines the endoscope's workspace. The method simulates possible insertions of the endoscope by creating a spatial tree. The growth of the spatial tree can be restricted by a series of filter functions. The filters enforce the internal and external constraints, given by the endoscope and organ properties. A model B is provided for describing the bending process of the endoscope's tip. With model B, the parameters needed to align the tip with the biopsy target can be determined.

It is to be understood that the present invention may be implemented in various forms of hardware, software, firmware, special purpose processors, or a combination thereof. Preferably, the present invention is implemented as a combination of hardware and software. Moreover, the software is preferably implemented as an application program tangibly embodied on a program storage device. The application program may be uploaded to, and executed by, a machine comprising any suitable architecture. Preferably, the machine is implemented on a computer platform having hardware such as one or more central processing units (CPU), a random access memory (RAM), and input/output (I/O) interface(s). The computer platform also includes an operating system and microinstruction code. The various processes and functions described herein may either be part of the microinstruction code or part of the application program (or a combination thereof) that is executed via the operating system. In addition, various other peripheral devices may be connected to the computer platform such as an additional data storage device and a printing device.

It is to be further understood that, because some of the constituent system components and method steps depicted in the accompanying Figures are preferably implemented in software, the actual connections between the system components (or the process steps) may differ depending upon the manner in which the present invention is programmed. Given the teachings herein, one of ordinary skill in the related art will be able to contemplate these and similar implementations or configurations of the present invention.

An important design criteria for models E and B is accuracy. The accuracy of a model directly affects the quality of the parameter estimation, and therewith the success rate of the guided biopsy. In contrast, model computation time plays a lesser role, since calculations can be done in a planing phase prior to an intervention.

Figure 1:
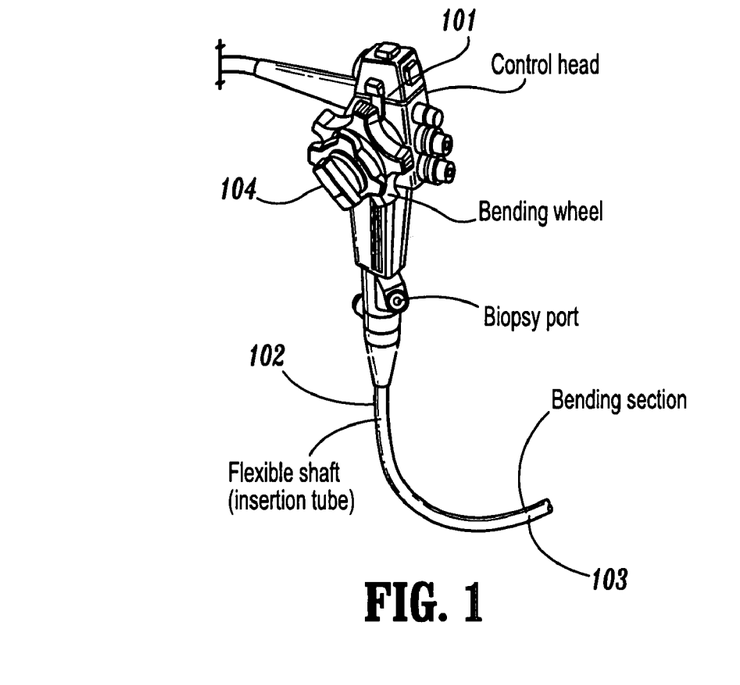
FIG. 1 is a diagram of a flexible endoscope according to an embodiment of the present invention.

A flexible endoscope is a surgical instrument that uses, for example, fiberoptics or a CCD camera to allow the surgeon to look inside the human body. Referring to FIG. 1, an endoscope comprises four basic components: a control head 101, shaft (insertion tube) 102, working (biopsy) channel and bending section 103. For the surgeon to have no lag between twisting the endoscope head and the rotation of the optical system in the tip, an endoscope shaft 102 has high torsional stiffness.

The transition of the shaft 102 into the bending section 103 is realized by a rigid sleeve (1). It follows a chain of links that allows the active bending of the tip (2). The chain connects to another rigid sleeve that can include an optical system (3). The bending section 103 has a larger diameter than the endoscope shaft 102.

The angle of the bending section 103 can be controlled by pull-wires running through the endoscope's shaft 102 to the bending wheel 104, located at the control head. The surgeon turns the bending wheel 104 to actively control the endoscope's path, to "look-around" and to guide a biopsy needle to the target.

According to an embodiment of the present invention, a TBNA can be based on a preoperative calculation of a "TBNA-protocol". The protocol can comprise four patient specific parameters. The estimation of these parameters $(1; p_2; p_3; p_4)$ can be based on the calculation of the endoscope's workspace:

1. Physician plans biopsy site S.
2. Calculation of endoscope length l to reach S: $l = A_E(S)$ 3. Calculation of the endoscope-workspace W to reach S with length l: $W=A_E(l; S)$.

4. For all w 0 W: Calculation of $p_2;p_3;p_4=B(w)$

For the determination of B(w), for each endoscope shape three parameters can be determined (needed to align the tip with the target) on the basis of the digital bending section model B. Where a parameter describes the endoscope's rotation about the shaft (twist), such as the example above, it can be important for the endoscope model to have substantially the same torsional stiffness.

As mentioned above, given that parameters can be angles, (two of the four parameters in the example above) accuracy can be important. Summarizing the physical properties of an endoscope; A model E should take the following internal constraints of an endoscope into account, for example, (1) shaft geometry like length and diameter, (2) shaft behavior like flexibility (3) torsional stiffness, (4) bending section geometry like length of the sleeves and length of the part, (5) bending section behavior under "active" bending.

Method $A_E$ modeling the external constraints can include the determination of: (1) the interaction of the entire endoscope with the organ, (2) the length l to the biopsy site S, (3) the endoscope's workspace W and (4) the restriction of W to the branch of interest (branch that includes S).

An endoscope comprises several mechanical parts, like flexible tubes and rigid sleeves. A model according to the present invention has been developed using a mechanical approach. An endoscope model E models an endoscope as a chain of rigid links, interconnected by discrete ball and socket joints. A link can be represented by a cylinder of a given length and a given diameter.

With this approach, the length of the links and the joint range determines the flexibility. The endoscope shaft and the part of the bending section are modeled in substantially the same way, with a different flexibility and diameter. The bending section sleeves are links at a specific position, with a given length and diameter.

The external constraints of the model are considered. The 20 insertion of an endoscope into an organ can be simulated by method $A_E$, which is based model E. The method recursively (depth-first search) creates a spatial tree under a set of given geometrical constraints. A spatial tree is a tree data structure, where each node represents a joint in 3D space. Each edge that connects a node with its child represents a link in 3D space. Each path from the root to a leaf represents a chain of links and therewith an endoscope. All paths from the root to the leafs represent the workspace of the modeled endoscope under the given constraints.

Constraints can be implemented by a series of filters. Each filter restricts the growth of the spatial tree and therewith the possible shapes an endoscope can take. For example a joint filter controls the flexibility of the endoscope, a gravity filter enforces gravity and a geometry filter controls the interaction of the endoscope with the organ. A bounding tube filter restricts the spatial tree to the branch of interest and the choice between two stopping criteria filters determines the calculation of either W or l.

Once the endoscope workspace W is calculated, a model B can be applied to each endoscope representation. Model B describes the bending behavior of bending section.

A model according to an embodiment of the present invention can be described by defining a link, and based on the link introducing the set $\Lambda$ of all possible sets of links. Starting with the unstructured set $\Lambda$, constraints can be introduced stepwise that impose structure and narrow the number of possible configurations, which leads to a definition of a tube. One structure imposed on $\Lambda$ leads to the set of all chains C, which can be constrained to the set of all tubes T, so $T\_C\_\Lambda$. Based on T, a bending section can be defined, and thus an endoscope can be defined as a length of bending sections.

Link l can be defined for a model according to the present invention. Let $$M=\{(a_{ij})|i,j=0,\ldots,3, a_{ij}\in R\}$$

be the set of all 4×4 matrices over R. A matrix F 0 M can be a representation (homogenous transform) of a reference frame in 3D space. A link $$l=(F; s; d); F\ 0\ M; s; d\ 0\ R \tag{1}$$

can be represented by a reference frame F attached to a cylinder with length s and diameter d. Reference frame F is attached to the cylinder such that the frame's z-axis is the centerline of the cylinder. The cylinder's bottom and top bases lie in the z=0 and z=s-plane. Assuming that all reference frames are known with respect to a world coordinate system $F_w$: $^{Fw}F, \forall F0M$.

The method assumes that the introduction of a link l implicates the introduction of it's components F: s and d. The set of all links can be denoted as:

$$L=\{l=(F;s;d)|F0M;s;d0R\} \tag{2}$$

and the power set of L, as the set of all subsets of L as:

$$\ldots =P(L); \tag{3}$$

A Collection of links $A\in A$ can be called, with n=|A| a collection of n links in $R^3$ with link length s and diameter d. A can be written as:

$$A=\{l_1=(F_1;s_1;d_1),\ldots,l_2=(F_2;s_2;d_2),\ldots,l_n=(F_n;s_n;d_n)\}$$

or, if the emphasize is more on the link frames, $A=\{F_1; F_2,\ldots,F_n\}$ with $F_i 0M$.

$\Lambda$, the set of all collections of links, does not impose structural constraints on the arrangement of the links. A set $C\_\ldots$ that includes only those link sets that describe a chain like structure can be determined. A collection of n links $C0\ldots$ is called a chain of length n, if the links in C satisfy certain conditions:

$$C0C\omega \tag{4}$$

$$C0\ldots$$

$$.|C|=n0N$$

$$.F_i(\hat{z}s_i)=F_{i+1}\vec{0}, \forall i=1,\ldots,n-1$$

$$.(s_i=s_j).(d_i=d_j), \forall l_i,l_j\in C$$

Note that the three 4×1 unit vectors can be denoted by $\hat{x},\hat{y},\hat{z}$ and the zero vector by $\vec{0}$. Condition $.|C|=n0N$ says that the top base of a cylinder should be connected to it's successor's bottom base. Condition $.F_i(\hat{z}s_i)=F_{i+1}\vec{0}, \forall i=1,\ldots,n-1$ says that all links in a chain should have the same length and diameter. To define a chain, parameters can be grouped in a 4-tuple $$c=(C;n;s;d) \tag{5}$$

A joint connects two adjacent links. If a joint allows a link only to be in a finite number of positions relative to its predecessor, it can be called a discrete joint. Formally a discrete joint can be described by a pair of links $$j=(l_1, l_2) \quad (6)$$

with a defined relation between $l_1$ and $l_2$. The set J of all joints that satisfy the joint specifications can be written as:

$$J_0=\{(l_1,l_2)|l_1=(F_1,s_1,d_1)0L, \quad (7)$$

$l_2=(F_2,s_2,d_2)0L$ and $F_2=R(\vec{v},2)F_1T(\hat{z}s)$; where $\vec{v} 0R_a=\{(xy0)^T|x,y\ 0\ R\}, 2\ 0\ R\}$ Note that T and R denote a 4×4 translation, respectively rotation matrix and that $R_a$ is the set of rotation axes. The specification of a joint says that the successor of a frame $F_1$ is given by translating $F_1$ by s along its z-axis and rotating it by 2 degrees about $\vec{v}$.

Figure 2A:
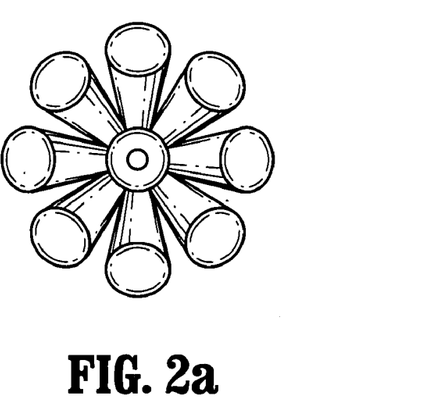
FIG. 2a is an illustration of possible endoscope tip positions according to an embodiment of the present invention.

For example: With $R_a=\{(xy0)^T|x,y0\{-1,0,1\}\}$, there are 9 rotation axes, 8 in the z=0-plane, equally spaced by 45 degrees. FIG. 2a shows the 9 possible positions a link $l_2$ can take relative to it's predecessor $l_1$ (occluded). Also note that 2 denotes the range of the joint, which is the angle between two adjacent links.

A method according to an embodiment of the present invention comprises a flexibility function, f~. The flexibility function imposes structure on a chain by introducing the notion of flexibility. The flexibility of a chain can be determined by the link length s and the maximal joint range $\hbar_{MAX}$. A flexibility function can be implemented that derives a joint range from a given link length and an intuitive flexibility value r$\chi$R. The idea of flexibility is related to the notion minimal radius, in the sense that the more flexible an endoscope is, the smaller the minimal radius of a circle one can form with the endoscope.

Figure 2B:
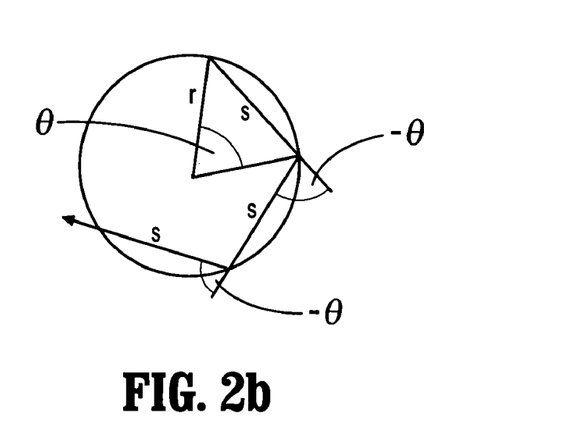
FIG. 2b is a circle approximated by segments according to another embodiment of the present invention.

As shown in FIG. 2b, a circle can be linear approximated by segments. Given a circle of radius r and the length s of each segment then the absolute value of the angle $\hbar$ between two segments is the same as the angle at the center. This angle defines the maximal joint range $\hbar_{MAX}$ dependent of r and s and is given by the flexibility function:

$$f\in:(R,R)\tau R, \text{ with} \quad (8)$$

$$f\in(s,r) = 2\sin^1\left(\frac{s}{2r}\right)$$

As described above, a chain is a collection of links, with no other constraint regarding the relation between two adjacent links than that they are connected. A flexible tube like structure can be defined by inserting joints between two adjacent links of a chain.

Regarding a set T_C_ ... that includes only those link sets that describe a collection of links interconnected by joints, a chain T 0 C is called a tube with length n and r if the links in $T=\{l_1,l_2,\ldots,l_n\}$ satisfy the following conditions:

T 0 T, (9)

T 0 C $.|T|=n\chi N$ $.(l_i,l_{i+1})\chi J\hbar, \ldots, i=1,\ldots,n-1$ $.0[\hbar|\hbar_{MAX};$ where $.\hbar_{MAX}=f\in(s,r)$ The third condition says that two adjacent links satisfy the joint constraint. The fourth condition defines the joint range between two consecutive links. It says that the angle between two adjacent links should not exceed the maximum joint range $\hbar_{MAX}$. All parameters describing a flexible tube can be grouped in a 5-tuple:

$$t = \left(T, \frac{li}{n,s}, d, r\right) \quad (10)$$

Note that n and s should be chosen, so that $ns=l_t$, the desired tube length.

A bending section b comprises two links interconnected by a flexible tube:

$$b=(l_f; t;l_1) \quad (11)$$

where $l_f\ 0\ L$ is the first link, $l_1\ 0\ L$ is the last link and t=(T,n,s,d,r) is a tube with flexibility r. Let $T=\{l_1,l_2,\ldots,l_n\}$, then the constraints for a bending section are:

b is a bending section ω (12)

$d_f=d=d_1$;

$.(l_f,l_1)\ 0\ J_2$ $.(l_n,l_1)\ 0\ J_2$ $.2=f\in(s,r)$

The condition $d_f=d=d_1$ says that all links of the bending section have the same diameter. The conditions $.(l_f,l_1)0J_2$ & $.(l_n,l_1)0J_2$ says that the first (last) link of the bending section is connected to the first (last) link of the flexible tube via a discrete joint. The condition $.2=f\in(s,r)$ says that the joint ranges of $l_1$ and $l_2$ are the same as the joint range of the flexible tube.

An endoscope is a flexible tube, connected to a bending section, via a discrete joint:

$$e=(t,b), \quad (13)$$

where t=(T,n,s,d,r) a flexible tube, and $b=(l_{fb},t_b,l_{fb})$ a bending section.

e is an endoscope ω (14)

$(l_n,l_{fb})\ 0\ J_2$ $.2=f\in(s,r)$

A real endoscope has a high torsional stiffness, since twisting the endoscope head by ∀ degrees leads to a rotation of the tip camera by ∀ degrees. A piecewise linear tube is maximal torsional stiff if there is no rotation about the z-axis in between any two adjacent links. An endoscope $e_r\ 0\ E_r$ has a maximal torsional stiffness. Let $T=\{F_1,\ldots,F_n\}$ be the insertion tube of the endoscope. Each sub tube $T_s(i)T$, with $T_s(i)=\{F_1,F_2,\ldots,F_i\}$, i=1,...,n is torsionally stiff. Proof by induction:

1. (basis of induction): A single link $T_s(i)$ is torsionally stiff.

2. (inductive step): Given that $T_s(i)$ is torsionally stiff. Let $j=(l_i,l_{i+1})$, $j\chi J_2$ be the next joint in the chain. From (7) can be seen that the rotation between F i and F i+1 is given by $F_{i+1}=R(\vec{v},\theta)F_i$, where $\vec{v}\in R_a$. Since all vectors in $R_a$ have a 0 z-component, there is no rotation about the z-axis. It follows that $T_s(i+1)$ is torsionally stiff.

According to an embodiment of the present invention, a model can determine external constraints. Including, for example geometry O and Gravity Fn. G. The geometry of an organ can be described as a subset of the 3D-space and the gravity unit vector as given with respect to the world coordinate system:

$$O \subset R^3 \text{ and } {}^{Fw}\vec{g} \in R^3 \quad (15)$$

A gravity function g can be assigned a scalar gravity value to a link that represents the link's projection (dot product) onto the gravity vector:

$$g: L \to R \quad (16)$$

$$g(l) = F\hat{z} \cdot \vec{g}$$

Experiments with an endoscope and a lung phantom showed that the endoscope generally remains stiff under insertion into the tracheobronchial tree. However, external force, like the collision of the endoscope with the organ walls, causes the endoscope to bend locally. The bending behavior of an endoscope model is determined by the behavior of the joints. The bending behavior of an endoscope model can be characterized by specifying the joint properties. The maximum joint range $\hbar_{MAX}$ determines the flexibility of the endoscope. However, a collision at the endoscope's tip will not immediately cause the involved joints to bend to their maximum range. More likely the force caused by the collision will be distributed among the adjacent joints. This behavior can be modeled with a joint range function $$f\hbar_{max}: N \delta R \text{ with } 0[f\hbar_{max}[\hbar_{MAX} \quad (17)$$

and a "joint rate" function $$f\hbar: N \delta R \text{ where } 0[f\hbar[f\hbar_{max}: \quad (18)$$

Figure 3A:
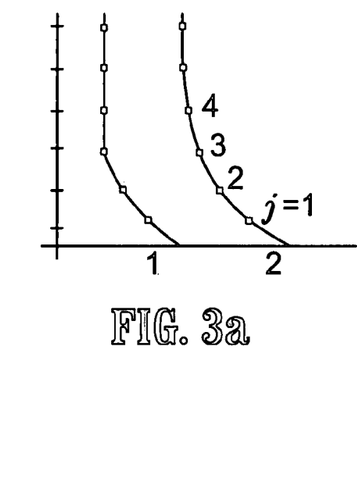
FIG. 3a is a graph of two different bending behaviors according to an embodiment of the present invention.
Figure 3B:
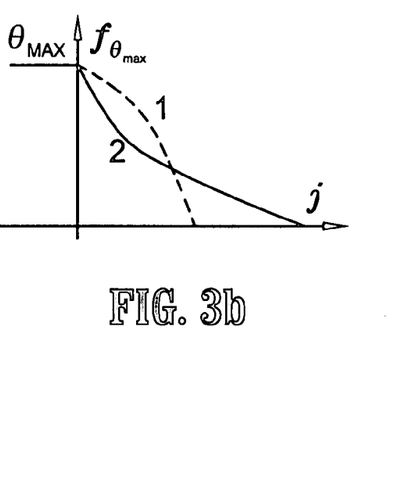
Figure 4A:
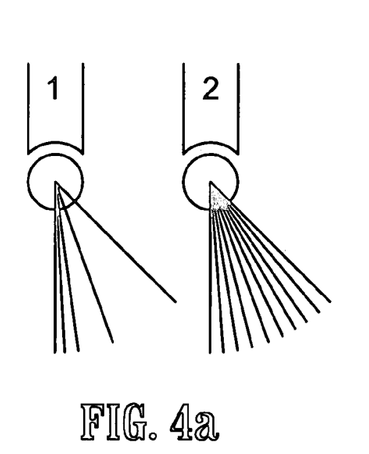
FIG. 4a is an illustration of two joints with different rotation rates according to an embodiment of the present invention.
Figure 4B:
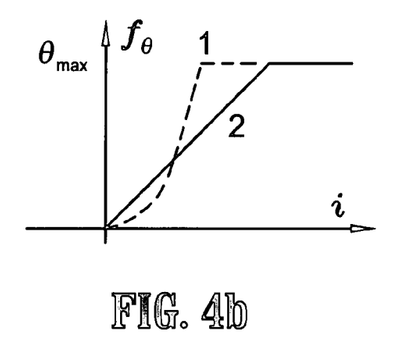

The first describes the maximum joint range $\vartheta_{max}$ [$\vartheta_{MAX}$ of an individual joint in dependency of the distance of this joint to the collision. The second function describes the steps (rate) $\vartheta$ in which an individual joint turns until its maximum joint range ($\vartheta[\vartheta_{MAX}$) is reached. FIGS. 3a and 3b show two different bending behaviors induced by the corresponding joint range functions on the right. FIGS. 4a and 4b show two joints with different angle rates and the corresponding joint rate functions.

To describe the geometry of a link, the link can be approximated by a set $S_{s,d}$ $R^3$ of sample points on its surface, link sample points. Let $\vec{s} = (xyz)^T \in R^3$:

$$\vec{s} \in S_{s,d} \Leftrightarrow, 0 \leq z \leq s \land \sqrt{x^2 + y^2} \leq \frac{d}{2} \quad (19)$$

For a real endoscope $e_r$, let E be the set of all endoscopes:

$$E = \{e = (t,b) | t = (T,n,s,d,r), \quad (20)$$

$$b = (l_{fb}, t_b, l_b),$$

$$t_b = \{T_b, n_b, s_b, d_b, r_b\}\}$$

A set of endoscopes $E_r \chi E$ is called the set of all real endoscopes, if an endoscope $e_r$ satisfies certain constraints:

$$e_r \in E_r, \Leftrightarrow, \quad (21)$$

$$e_r \in E$$

$$\Lambda F_i \vec{s} \in O, \wp \vec{s} \in S_{s,d}, \wp i-1, \ldots, n$$

$$\Lambda 1_i \in Y_i, \wp 1_i \in T, \text{ where } Y_i \subset X_i, \text{ with}$$

$$Y_i = \{l \in X_i | \{\hat{1} \in X_i | g(\hat{1}) \geq g(1)\} | \leq 3\}$$

$$X_i = \{\overline{1} \in L | (1_{i-1}, \overline{1}) \in J_\theta\}$$

The constraint $e_r \in E$ says all links to be collision free with the organ. The constraint $$\Lambda F_i \vec{s} \in O, \wp \vec{s} \in S_{s,d}, \wp i-1, \ldots, n$$

$$\Lambda 1_i \in Y_i, \wp 1_i \in T, \text{ where } Y_i \subset X_i, \text{ with}$$

$$Y_i = \{1 \in X_i | \{\hat{1} \in X_i | g(\hat{1}) \geq g(1)\} | \leq 3\}$$

$$X_i = \{\overline{1} \in L | (1_{i-1}, \overline{1}) \in J_\theta\}$$

considers for a link $l_i$ the set $X_i$ of all successors of link $l_{i-1}$. Note that $l_i \chi X_i$. The constraint says that each link $l_i$ of a real endoscope is among a set of links $Y_i$ which represents the three links with the greatest gravity values $g(1)$ of all links in $X_i$. With other words, considering endoscopes whose links are among the respective three links with the greatest projection on the gravity vector. Parameters that describe a real endoscope can be grouped in a 6-tuple, a endoscope model E:

$$E = (e_r, f_{\theta max}, f_\theta, O, {}^{Fw}\vec{g}, S_{s,d}) \quad (22)$$

Figure 5:
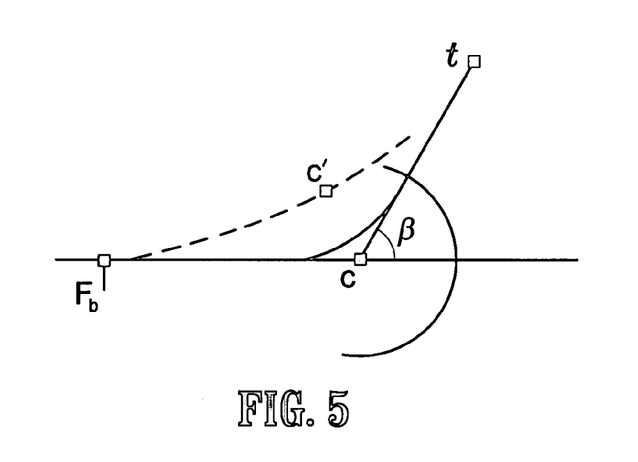
FIG. 5 is an illustration of a model according to an embodiment of the present invention.

According to an embodiment of the present invention, an endoscope model can take the passive bending of the bending section into account that is caused by interaction with the organ walls. A model B describes the active bending behavior of the bending section, caused by the surgeon, rotating the bending wheel. Experiments showed that the bending movement of the straight tip to the left and right can be approximated by a semicircle with its center c=49 mm away from the endoscope's end. FIG. 5, shows the distal end of an endoscope, including the first link $l_{fb}$ of the bending section, target t and semicircle center c. The figure shows that the sought bending angle of a straight bending section can be approximated by the angle ↕ between t and unit vector $\hat{z}$ of link C that includes c. If the bending section is bent to the dashed shape, without using the bending wheel, but an external force, the same wheel angle ↕ is obtained. This cannot be geometrically explained on the basis of the figure, but is a result of the pull wire mechanics. This effect can be modeled by calculating ↕ based on a straight bending section, even though the bending section may be curved.

In order to find "real endoscopes" that satisfy the internal and external constraints, possible configurations can be enumerated, beginning with a given start link 1*. This approach can be implemented as a recursive backtracking method:

attachLink:
  Input: Link 1*χL, Recursion depth c
  Global: collisionAt=1
  Return: TRUE, if the current link has at least one successful successor, else FALSE
  Output: Real endoscope $e_r \chi E_r$
  The method attachLink can be written as follows:

```
1:    i = 0
2:    E = □
3:    c = c + 1
```

-continued

```
4:      LOOP
5:          j = collisionAt c
6:          i = i + 1
7:          ℏ_max = fℏmax (j)
8:          ℏ = fℏ(i)
9:          L_1 = f_1 (L, ℏ)  // discrete joint
10:         L_2 = f_2 (L_1)    // organ geometry
11:         L_3 = f_3 (L_2)    // gravity
12:         L_4 = f_4 (L_3)    // bounding tube
13:         L_5 = f_5 (L_4)    // stopping criteria
14:         IF( |L5| > 0)
15:             E = E 4 L_5
16:             RETURN (TRUE)
17:         successCount = 0
18:         ∀1 χ L_4:
19:             IF (attachLink(1, c))
20:                 successCount = successCount +1
21:                 E = E 4 1
22:         WHILE (successCount = 0) · (2 < 2_max)
23:         IF (successCount = 0)
24:             collisionAt = c
25:         RETURN (successCount > 0)
```

Statements in this formulation of AE that manage the creation of the tree data structure (nodes and pointers) have been omitted. The above pseudo-code is provided as an example, and one of ordinary skill in the art will appreciate that the method can be embodied in various forms of code.

The method includes a loop from line 4 to line 22 that executes the joint rotation. As illustrated in FIG. 4, the rotation angle (for each rotation axis in $R_a$) is increased stepwise, until a position is determined at which a link can be attached. By starting rotating away from the straight center link in the directions given by the rotation axis (like an opening rose, see FIG. 2a), an endoscope with high stiffness that only bends locally to resolve a collision can be determined.

To calculate $2_{max}$, the distance j of the current joint to the link that caused a collision (see FIG. 3) is calculated in line 5.

In Lines 9-13 the set of all links L is passed through a series of filters (5.1), to find the successors of the current link l*.

If there are links that passed filter $f_5$, which implements the stopping criteria, these links can be added to the endoscope and leave the recursion (line 14-16). If not, the links that passed filter $f_5$ represent the links that satisfy all constraints, but have not reached the target yet. With each of those links, the recursion can be called to continue attaching links (line 19).

The joint filter can be expressed as:

$$f_1(L,\theta)=\{l\in L|(l^*,l)\in J_\theta\}$$

Depending on the recursion depth c, the filter generates shaft links, sleeve links or bending section links: Let l=(F,s,d) be a link generated by filter $f_1$:

$$s = \begin{cases} s_s : 0 \leq c \leq n_s & \text{shaft} \\ s_{f_b} : c = n_s + 1 & \text{first sleeve} \\ s_b : n_s + 2 \leq c \leq n_s + n_b & \text{flex. bending} \\ s_{lb} : c = n_s + n_b + 2 & \text{last sleeve} \end{cases}$$

$$d = \begin{cases} d_s : 0 \leq c \leq n_s & \text{shaft} \\ d_b : n_s + 1 \leq c \leq n_s + n_b + 2 & \text{bending sec.} \end{cases}$$

The geometry filter can be written as:

$$f_2(A)=\{1\in A|\vec{F s}\in O, \vec{\varsigma s}\in S_{s,d}\}$$

A collision detection method can also be implemented. For example, a collision detection method that determines, for a given point in 3D space, whether the point lies inside or outside the geometry of interest, e.g., a tracheobronchial spatial tree.

The gravity filter can be written as:

$$f_3(A)=\{1\in A|\{1\in A|g(\hat{1})\geq g(1)|\leq 3\}\}$$

The workspace of an endoscope inserted into a tree-like structure like the bronchus can generally reach into many branches. However, for the purpose of guiding a TBNA, a method, and in particular, the bounding filter, considers that part of the workspace that reaches into the branch of interest (target branch). Let a path from the beginning of the trachea to the planned biopsy site S be given by a list of k pairs $\vec{c}\in R^3, d\in R$, where $\vec{c}$ is a point on the path and d the corresponding diameter of the contour of the slice that is closest to $\vec{c}$:

$$f_4(A)=\{1\in A|\|\vec{F 0}-\vec{c_i}\|\leq d_p, i=1,\ldots,k\}$$

The stopping criteria for workspace calculation can be the overall number N of links, needed to reach the biopsy site, so $N=n+1+n_b+1$ (shaft links plus bending links plus two sleeve links):

$$f_5(A) = \begin{cases} A : c = N \\ 0 : \text{else} \end{cases}$$

Stopping criteria for calculating l is fulfilled when a link l docks to the target link $l_t$. Link l has docked to $l_t$ if l's start and end point lie inside $l_t$'s docking cone. The docking cone's origin is the origin of $F_t$, its main axis is the negative z-axis of $F_t$ and its base lies in $F_t$'s z=s-plane. The radius of the cone base is s tan 2:

$$f_5(A)=\{1\in A|((-s\leq p_z\leq 0)\wedge(\sqrt{p_x^2+p_y^2}\leq\tan(\theta)p_z))_p \vec{p}\in\{\vec{q},\vec{r}\}\}^p \text{ where}$$

$$\vec{q}=F_1^{-1}\vec{F 0}, \vec{r}=F_i^{-1}F\hat{z}s, \vec{p},\vec{q},\vec{r}\in R^3$$

An embodiment of the present invention has been implemented on a SGI PC540, 550 Mhz (single), 0.5 GB RAM, running Windows 2000 and OpenGL. A lung phantom using transparent PVC tubes was used for testing. Thirty-seven marker sticks were randomly placed as artificial targets in the model. The phantom was then scanned (512×512×382, 1 mm slice distance, 1.2 thickness) and a model of the tracheobronchial tree was reconstructed. Endoscope: OLYMPUS GIF 100 Videoscope.

The accuracy of the endoscope model reflects the behavior of an OLYMPUS GIF 100 videoscope. The model was compared to the real endoscope parameters needed to hit a marker in the lung phantom to the estimated parameters derived from a model AE. Out of all 37 markers, 5 were chosen as biopsy targets. For each target, the TBNA was executed 20 times and the four parameters needed to touch the marker stick with the biopsy needle were recorded. Furthermore, the parameters for the same 5 targets were estimated by using the implementation of AE and B.

For example, the input parameters of model E were specified to represent the GIF 100 videoscope. It's bending section is 25+35+35=95 mm long. For this target the insertion depth was planned to be 223 mm, so that the insertion tube needs to be 128 mm long:

$$e_{GIF100} = (t, b) \qquad b = (I_{fb}, t_b, I_{lb})$$

$$t = \left(T, \overline{\frac{128\,mm}{8,16}}, 9,200\right) \qquad I_{fb} = (F, 2, 1)$$

$$t_b = \left(T, \overline{\frac{35\,mm}{3,11.6}}, 11,280\right) \qquad I_{lb} = (F, 2, 1)$$

$$R_a = \left\{ \begin{pmatrix} x \\ y \\ 0 \end{pmatrix} \mid x, y \in \{-1, 0, 1\} \right\} \quad \theta_{MAX} = f \sim (16,200)$$

$$f_{\theta max}(j) = -\frac{\theta_{MAX}}{5} j + \theta_{MAX} \qquad f\theta(i) = \frac{\theta_{MAX}}{3} i$$

Computation time was 2.6 minutes for building the entire spatial tree with a recursion depth of 13 links.

The average error between the respective estimated and experimentally obtained alignment parameter is 12°, 3° and 1 mm. By applying an error model to these variations, the individual errors can be translated into a more general statement: In the average case a model according to the present invention can hit targets of about 13 mm in diameter.

To demonstrate the versatility of a model according to the present invention, a model was used to simulate the insertion of a catheter into a brain artery. A catheter is a very thin, highly flexible tube used, among others to place stints for the treatment of aneurysms. To show that a model can even represent a catheter, input parameters were specified as:

$$e_{cath} = (t, b) \qquad b = (I_{fb}, t_b, I_{lb})$$

$$t = \left(T, \overline{\frac{68\,mm}{34,2}}, 1, 25\right) \quad I_{fb} = (F, 2, 1)$$

$$t_b = \left(T, \overline{\frac{68\,mm}{1,2}}, 1, 25\right) \quad I_{lb} = (F, 2, 1)$$

Note that in opposition to $e_{GIF}100$ the parameters for the bending section were chosen to be identical to the shaft parameters, which effectively means that $e_{cath}$ has no bending section. To demonstrate its torsional stiffness, in each cylinder frame the same two lines were drawn, parallel to the cylinder's z-axis. The catheter is 74 mm long, comprises 37 links and was computed in 8.0 minutes. The right figure shows the catheter's workspace for a length of 38 mm. Computation time here was 7.3 minutes for building the entire spatial tree consisting of 289 leafs/endoscopes. The recursion depth/endoscope length is 19 links.

Figure 6:
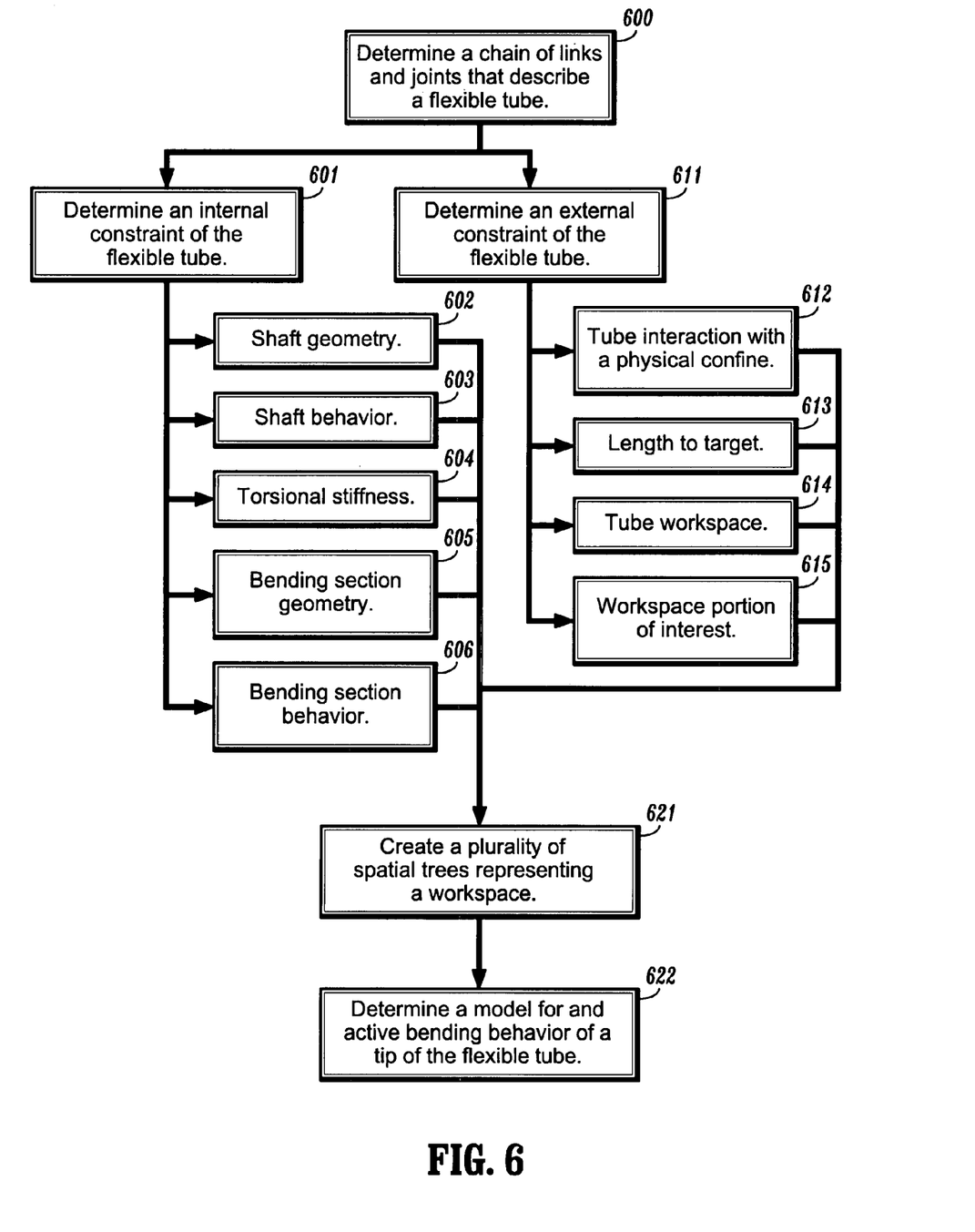
FIG. 6 is a flowchart of a method according to an embodiment of the present invention.

Referring to FIG. 6, an overview of a method according to an embodiment of the present invention is shown. A flexible tube is described as a chain of links and joints 600. The method determines at least one internal constraint 601, for example, a shaft geometry 602, a shaft behavior 603, a torsional stiffness 604, a bending section geometry 605, and a bending section behavior 606. The method determines at least one external constraint 611, for example, interactions between the tube and a physical confine 612 (e.g., as between the models of the tube and the organ), a length to a target 613, a tube workspace 614, and a workspace portion of interest 615. From the constraints or filters, a spatial tree is grown 621. An active bending model of the tip of the flexible tube can be implemented 622, which can, for example, model the alignment of the flexible tube relative to a target.

Having described embodiments for a method of simulating a flexible tube, it is noted that modifications and variations can be made by persons skilled in the art in light of the above teachings. It is therefore to be understood that changes may be made in the particular embodiments of the invention disclosed it which are within the scope and spirit of the invention as defined by the appended claims. Having thus described the Be invention with the details and particularity required by the patent laws, what is claimed and desired protected by Letters Patent is set forth in the appended claims.

What is claimed is:

1. A computer-implemented method of modeling an endoscope comprising the steps of:
    representing the endoscope as a chain of rigid links, interconnected by discrete joints;
    determining filter functions including a plurality of internal constraints of the endoscope and a plurality of external constraints of the endoscope, wherein the filter functions comprise at least one of a geometry filter, a joint filter, a bounding tube filter, a gravity filter, and a stopping criteria filter;
    determining a spatial tree corresponding to the endoscope limited by the plurality of internal constraints and the plurality of external constraints of the endoscope, wherein the plurality of internal constraints and the plurality of external constraints are applied to each of the rigid links individually;
    determining a model of the active bending behavior of the tip of the endoscope, comprising
        determining the center of a circle of radius r that defines a movement of the tip of the endoscope; and
    storing the spatial tree and the model of the active bending behavior on a computer readable media.

2. The computer-implemented method of claim 1, wherein the spatial tree is a tree data structure comprising a plurality of nodes, wherein each node represents a discrete joint of the endoscope in three-dimensional space.

3. The computer-implemented method of claim 1, wherein the spatial tree is a tree data structure comprising a plurality of edges, wherein each edge connects a node with its child and represents a rigid link in three-dimensional space.

4. The computer-implemented method of claim 1, wherein the spatial tree is a tree data structure comprising a plurality of paths, wherein each path from a root to a leaf represents a volume that may be occupied by the endoscope.

5. The computer-implemented method of claim 1, further comprising the step of building the spatial tree, wherein building the spatial tree comprises the steps of:
    determining an interaction of the endoscope with the environment represented by the external constraints;
    determining a length of the endoscope to a target as a first internal constraint;
    determining a length for each link of the endoscope as a second internal constraint;
    determining a diameter for each link of the endoscope as a third internal constraint;
    determining a maximum angle for each joint of the endoscope as a forth internal constraint; and
    restricting the spatial tree to a portion of the environment according to at least one of the first through forth internal constraints.

6. The computer-implemented method of claim 1, wherein the spatial tree is built one of recursively and iteratively.

7. A computer-implemented method of modeling a workspace of a an endoscope comprising the steps of:
provide a model of a physical confine;
determining a joint filter according to a flexibility of the endoscope;
determining a geometry filter according to an interaction of the endoscope with the model of the physical confine;
determining a gravity factor;
determining a bounding tube filter according to a portion of the model of the physical confine in which the endoscope has been inserted;
determining a stopping criteria filter according to one of a dock or a tube length; and
determining a model of the workspace of the endoscope according to the joint filter, the geometry filter, the gravity filter, the bounding tube filter, and the stopping criteria filter; and
storing the model of the workspace of the endoscope on a computer readable media.

8. The computer-implemented method of claim 7, wherein the step of determining a joint filter comprises determining a maximum joint angle according to a position of a joint within a chain of interconnected links, wherein the endoscope is modeled as the chain of interconnected links.

9. The computer-implemented method of claim 7, further comprising the step of determining a model of the physical confines.

10. The computer-implemented method of claim 7, wherein the step of determining a bounding tube filter limits the workspace to a portion of the physical confines.

11. The computer-implemented method of claim 7, wherein the stopping criteria is a number of links of the endoscope needed to reach a target site.

12. The computer-implemented method of claim 7, wherein the stopping criteria is fulfilled upon determining a dock between a link and the target site.

* * * * *

UNITED STATES PATENT AND TRADEMARK OFFICE
CERTIFICATE OF CORRECTION

PATENT NO. : 7,277,833 B2
APPLICATION NO. : 10/102580
DATED : October 2, 2007
INVENTOR(S) : Markus Kukuk Page 1 of 1

It is certified that error appears in the above-identified patent and that said Letters Patent is hereby corrected as shown below:

Item [54] in the title of the invention appearing at col. 1, line 1, the word "PENDING" should be changed to --BENDING-- so that the title of the invention appears as follows:

MODELING OF THE WORKSPACE AND ACTIVE BENDING BEHAVIOR OF AN ENDSCOPE USING FILTER FUNCTIONS

Signed and Sealed this

Sixth Day of October, 2009

David J. Kappos
*Director of the United States Patent and Trademark Office*